US012806052B2

(12) United States Patent
Osaka

(10) Patent No.: US 12,806,052 B2
(45) Date of Patent: Nov. 24, 2026

(54) CARTRIDGE SYSTEM

(71) Applicant: Olympus Corporation, Tokyo (JP)

(72) Inventor: Shingo Osaka, Tokyo (JP)

(73) Assignee: Olympus Corporation, Tokyo (JP)

(*) Notice: Subject to any disclaimer, the term of this patent is extended or adjusted under 35 U.S.C. 154(b) by 975 days.

(21) Appl. No.: 18/046,361

(22) Filed: Oct. 13, 2022

(65) Prior Publication Data

US 2023/0053606 A1 Feb. 23, 2023

Related U.S. Application Data

(63) Continuation of application No. PCT/JP2020/016971, filed on Apr. 17, 2020.

(51) Int. Cl.
*A61F 2/966* (2013.01)
*A61F 2/95* (2013.01)

(52) U.S. Cl.
CPC ............ *A61F 2/966* (2013.01); *A61F 2/9517* (2020.05); *A61F 2002/9505* (2013.01)

(58) Field of Classification Search
CPC ........ A61F 2/9517; A61F 2/962; A61F 2/966; A61F 2/95; A61F 2/2427; A61M 25/002;
(Continued)

(56) References Cited

U.S. PATENT DOCUMENTS 5,035,686 A 7/1991 Crittenden et al.
5,626,604 A * 5/1997 Cottone, Jr. ............ A61F 2/958 606/1
(Continued)

FOREIGN PATENT DOCUMENTS

JP 02277464 A 11/1990
JP 05029543 4/1993
(Continued)

OTHER PUBLICATIONS

"International Application Serial No. PCT/JP2020/016971, International Search Report dated Jul. 7, 2020", (Jul. 7, 2020), 2 pgs.
(Continued)

*Primary Examiner* — Sarah W Aleman
*Assistant Examiner* — Paris Marie Blass
(74) *Attorney, Agent, or Firm* — Schwegman Lundberg & Woessner, P.A.

(57) ABSTRACT

A stent delivery system includes a stent; a pusher catheter disposed at a proximal-end side thereof; and a collet chuck disposed at the proximal-end side of the pusher catheter. The collet chuck includes a collet disposed along an outer circumference of a guide catheter; and a chuck nut provided to be relatively advanceable and retractable with respect to the collet and into which the guide catheter is insertable, and an inner circumferential surface of the chuck nut facing a center axis of the guide catheter includes a first region tightens the collet to make the collet to approach the center axis as coming into contact with the collet while approaching the collet; and a second region being at an opposite side of the collet with respect to the first region for making an approaching amount of the collet to be smaller than that in the first region.

16 Claims, 7 Drawing Sheets

(58) Field of Classification Search
CPC .......... A61M 25/0147; A61M 25/0133; A61M 2025/09125; A61M 2025/09116
See application file for complete search history.

(56) References Cited

U.S. PATENT DOCUMENTS

| | | | | |
|---|---|---|---|---|
| 2004/0034311 | A1* | 2/2004 | Mihalcik | A61B 1/00195 600/585 |
| 2005/0095891 | A1 | 5/2005 | Schorn | |
| 2007/0005122 | A1* | 1/2007 | Inoue | A61F 2/94 623/1.11 |
| 2007/0123971 | A1* | 5/2007 | Kennedy, II | A61F 2/95 623/1.11 |
| 2009/0105653 | A1 | 4/2009 | Spenser et al. | |
| 2011/0125133 | A1 | 5/2011 | Aggerholm et al. | |
| 2013/0030520 | A1* | 1/2013 | Lee | A61F 2/958 623/2.11 |
| 2013/0152659 | A1* | 6/2013 | Maimon | B21D 41/00 72/402 |
| 2021/0213257 | A1* | 7/2021 | Kotmel | A61M 25/09041 |

FOREIGN PATENT DOCUMENTS

| | | | |
|---|---|---|---|
| JP | 09173465 | | 7/1997 |
| JP | 2923298 | B2 | 7/1999 |
| JP | 2005131413 | A | 5/2005 |
| JP | 2014097103 | | 5/2014 |
| WO | WO-2017213139 | A1 | 12/2017 |

OTHER PUBLICATIONS

"Japanese Application Serial No. 2022-515182, Notice of Allowance dated Oct. 17, 2023", w English Translation, (Oct. 17, 2023), 5 pgs.

* cited by examiner

CARTRIDGE SYSTEM

CROSS REFERENCE TO RELATED APPLICATIONS

This application is a continuation of and claims the benefit of priority of PCT International Application No. PCT/JP2020/016971, filed Apr. 17, 2020. The contents of the PCT International Application are incorporated herein by reference.

TECHNICAL FIELD

The present disclosure relates to a stent delivery system.

BACKGROUND

Stent delivery systems deliver and indwells a stent at a desired location, such as a stenosis in the bile duct, through an endoscopic channel.

Stent Delivery systems generally include a chuck mechanism for clamping a guide catheter in an operation portion. The chuck mechanism is configured to determine a dimension in which the guide catheter is discharged from a distal end of the stent by clamping the guide catheter. Since a length of the stent varies depending on the procedures, the dimension in which the guide catheter is discharged from the distal end of the stent is adjusted according to the length of the stent.

Various mechanisms for clamping a tubular or a wire-shaped structure such as a guide catheter or a guide wire have are used. For example, in a medical guide wire described in Japanese Patent (Granted) No. 2923298, a wire main body is clamped and fixed by a chuck portion housed inside a front outer cylinder and a rear outer cylinder that are screwed with each other. By screwing the rear outer cylinder into the front outer cylinder, the inner wall surface of the distal-end portion of the rear outer cylinder moves while being in contact with the tapered outer surface of the chuck member. At this time, a slit forming portion is pushed toward a shaft-core hollow portion by the pressing of the rear outer cylinder to be contracted, and the wire main body is tightened from the surroundings such that the wire main body is clamped and fixed.

However, the medical guide wire described in Japanese Patent (Granted) No. 2923298 has a structure in which the slit forming portion is pushed toward the shaft-core hollow portion to be contracted as the rear outer cylinder is screwed into the front outer cylinder. A force by the slit forming portion to tighten the wire main body becomes excessively large when the rear outer cylinder is screwed too much with respect to the front outer cylinder, and the force becomes insufficient when the screwing is insufficient. Therefore, it is possible that the medical guide wire described in Japanese Patent (Granted) No. 2923298 cannot stably clamp the wire main body with an appropriate tightening force.

SUMMARY

According to an aspect of the present disclosure, A stent delivery system includes a stent; a pusher catheter disposed at a proximal-end side of the stent; and a collet chuck disposed at the proximal-end side of the pusher catheter, wherein the collet chuck includes a collet disposed along an outer circumference of a guide catheter being insertable into the stent and the pusher catheter; and a chuck nut provided to be relatively advanceable and retractable with respect to the collet and into which the guide catheter is insertable, and an inner circumferential surface of the chuck nut facing a center axis of the guide catheter includes a first region tightens the collet to make the collet to approach the center axis as coming into contact with the collet while approaching the collet; and a second region being at an opposite side of the collet with respect to the first region, wherein an approaching amount of the collet to the center axis as the second region coming into contact with the collet while approaching the collet to make the collet to approach the center axis is smaller than that in the first region.

DESCRIPTION OF EMBODIMENTS

A first embodiment of the present disclosure will be described with reference to FIG. 1 to FIG. 8. Hereinafter, in a stent delivery system, a side inserted into the stenosis portion will be referred to as a distal-end side, and a user side will be referred to as a proximal-end side.

A stent delivery system 100 according to the present embodiment is a system in which a stent 20 reaches a desired position such as the stenosis portion in the bile duct and is indwelled through an endoscopic channel.

Figure 1:
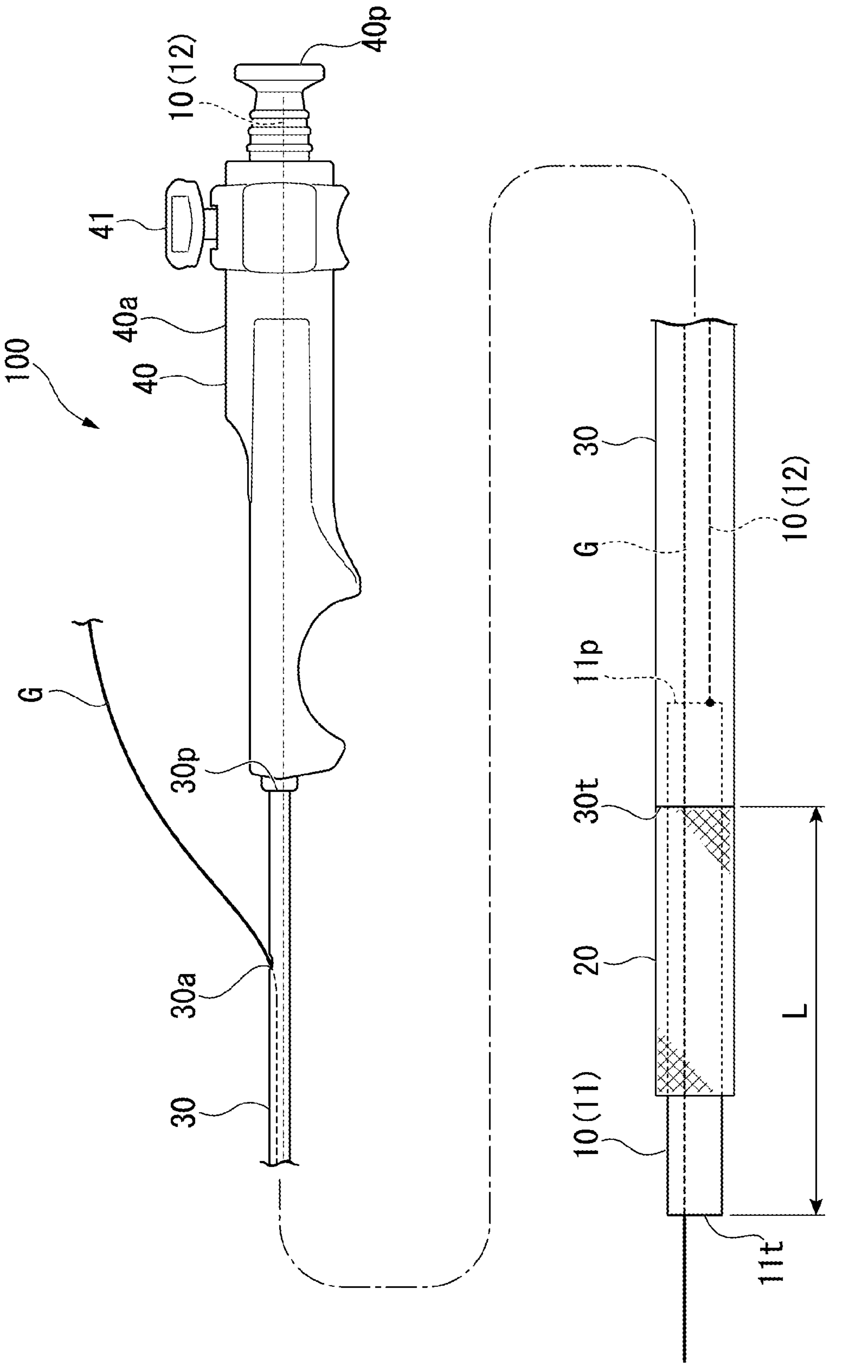
FIG. 1 is a side view showing a stent delivery system according to an embodiment of the present disclosure.

FIG. 1 is a side view showing the stent delivery system 100 according to the present embodiment. As shown in FIG. 1, the stent delivery system 100 includes a guide wire G, a guide catheter 10, the stent 20, a pusher catheter 30, and an operation portion 40.

The guide wire G guides the guide catheter 10, the stent 20, and the pusher catheter 30 to the stenosis portion. The guide wire G is introduced into the bile duct through the endoscopic channel. A distal end of the guide wire G is inserted to a position beyond the stenosis portion.

The guide catheter 10 assists the stent 20 to enter the stenosis portion. The guide catheter 10 has a catheter lumen 11 and an operation wire 12. The catheter lumen 11 is a tubular member made of resin or the like. The guide wire G is inserted through the catheter lumen 11. The guide catheter 10 is guided to the stenosis portion by the guide wire G.

The stent 20 is disposed on an outer circumference of the catheter lumen 11. With the stent 20 disposed, a distal end 11*t* of the catheter lumen 11 is exposed from the stent 20. In the guide catheter 10, the distal end 11*t* of the catheter lumen 11 is inserted into the stenosis portion earlier than the stent 20. The catheter lumen 11 widens the stenosis portion and assists the stent 20 to enter the stenosis portion.

The operation wire 12 pushes and pulls the catheter lumen 11 to move the catheter lumen 11 to the distal-end side and the proximal-end side. The operation wire 12 is connected to a proximal end 11*p* of the catheter lumen 11.

The stent 20 is a tubular member made of resin or the like. The stent 20 is disposed on the outer circumference of the catheter lumen 11 of the guide catheter 10. The stent 20 is joined and fixed to the catheter lumen 11.

The pusher catheter 30 indwells the stent 20 in the stenosis portion. The pusher catheter 30 is a tubular member made of resin or the like. The guide wire G and the guide catheter 10 are inserted into the pusher catheter 30. The pusher catheter 30 is arranged at the proximal-end side of the guide catheter 10 with respect to the stent 20.

An inner diameter of the pusher catheter 30 is larger than the outer diameter of the catheter lumen 11 of the guide catheter 10. The inner diameter and the outer diameters of the pusher catheter 30 are substantially the same as the inner diameter and the outer diameters of the stent 20, respectively. By pulling the guide catheter 10 toward the proximal-end side, the stent 20 fixed to the guide catheter 10 is pulled toward the proximal-end side. The stent 20 pulled toward the proximal-end abuts on the pusher catheter 30. When the guide catheter 10 is pulled toward the proximal end side with a force equal to or larger than a certain magnitude in a state in which the stent 20 and the pusher catheter 30 are in contact with each other, a force is generated between the stent 20 and the guide catheter 10 to separate them from each other. Since the force is generated between the stent 20 and the guide catheter 10 to separate them from each other, the stent 20 and the guide catheter 10 are separated from each other, and the fixation between the guide catheter 10 and the stent 20 is released.

When the guide catheter 10 is pulled toward the proximal-end side in the state in which the fixation between the guide catheter 10 and the stent 20 are released, the guide catheter 10 moves toward the proximal-end side. Since the stent 20 is pressed by the pusher catheter 30, the stent 20 does not move to the proximal-end side. The stent 20 is detached from the guide catheter 10 and indwelled at the current place.

A guide wire port 30*a* is formed on the outer circumferential surface of the pusher catheter 30 at a position between the distal end 30*t* and the proximal end 30*p*. The guide wire G is discharged from the guide wire port 30*a*.

The operation portion 40 clamps the guide catheter 10 extending from the proximal end 30*p* of the pusher catheter 30. The operation portion 40 clamps the guide catheter 10 and adjusts the length L of the guide catheter 10 being discharged from the distal end 30*t* of the pusher catheter 30.

Figure 2:
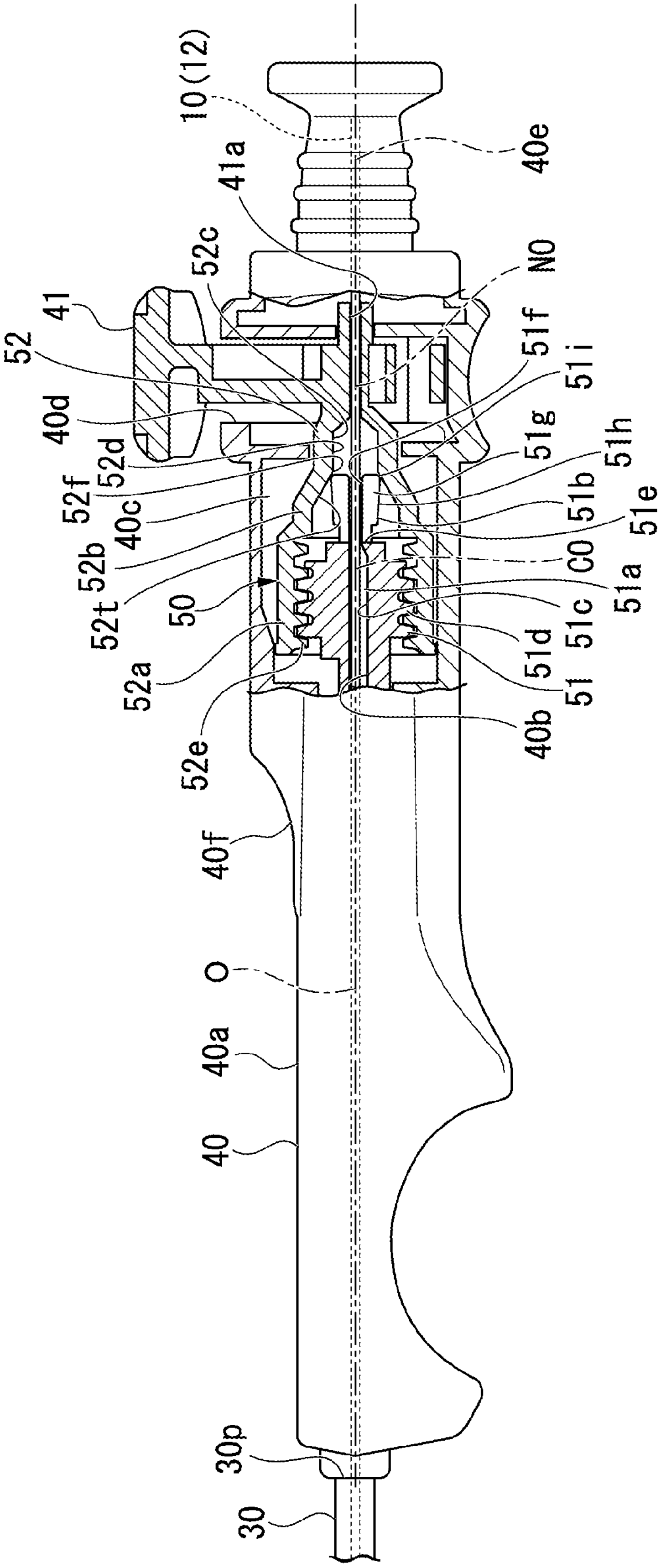
FIG. 2 is an enlarged cross-sectional view showing an operation portion of the stent delivery system in a state of releasing a guide catheter according to the embodiment of the present disclosure.

FIG. 2 is an enlarged view of the operation portion 40. The operation portion 40 pushes and pulls the pusher catheter 30 along the guide wire G. The operation portion 40 adjusts a position of the guide catheter 10 with respect to the pusher catheter 30. As shown in FIG. 2, the operation portion 40 includes a housing 40*a*, a lever 41, and a collet chuck 50. The collet chuck 50 has a collet portion 51 and a chuck nut 52.

As shown in FIG. 2, the housing 40*a* is provided at the proximal end 30*p* of the pusher catheter 30. The housing 40*a* is formed in a substantially cylindrical shape. A hollow portion of the housing 40*a* communicates with a hollow portion of the pusher catheter 30. The housing 40*a* includes a distal-end side hollow portion 40*b*, an internal space 40*c*, a notch portion 40*d*, and a proximal-end side hollow portion 40*e*. The distal-end side hollow portion 40*b*, the internal space 40*c*, and the proximal-end side hollow portion 40*e* communicate with each other.

The distal-end side hollow portion 40*b* is formed along a central axis O of the housing 40*a*. The distal-end side hollow portion 40*b* communicates with the hollow portion of the pusher catheter 30. The operation wire 12 of the guide catheter 10 extending from the proximal end 30*p* of the pusher catheter 30 is inserted into the distal-end side hollow portion 40*b*.

The internal space 40*c* is formed along the central axis O of the housing 40*a*. The internal space 40*c* is formed on the proximal-end side of the distal-end side hollow portion 40*b* and communicates with the distal-end side hollow portion 40*b*. The internal space 40*c* is formed closer to the outer circumferential surface 40*f* of the housing 40*a* than the front-end side hollow portion 40*b*. The operation wire 12 is inserted into the internal space 40*c*.

The notch portion 40*d* is formed on the outer circumferential surface 40*f* on the proximal-end side of the internal space 40*c*, and communicates the internal space 40*c* with the space outside the housing 40*a*. The notch portion 40*d* is formed over a range of approximately 90 degrees around the central axis O of the housing 40*a*.

The proximal-end side hollow portion 40*e* is formed along the central axis O of the housing 40*a*. The proximal-end side hollow portion 40*e* is formed on the proximal-end side of the internal space 40*c* of the housing 40*a* and communicates with the internal space 40*c*. The proximal-end side hollow portion 40*e* communicates with the space outside the housing 40*a*. The operation wire 12 is inserted through the proximal-end side hollow portion 40*e*.

The lever 41 switches between the fixed state and the released state of the guide catheter 10 by the operation portion 40. The lever 41 is integrally formed with the chuck nut 52 of the collet chuck 50, and the lever 41 rotates the collet chuck 50 to clamp and release the operation wire 12 to switch between the fixed state and the released state.

The lever 41 is arranged in the internal space 40*c* of the housing 40*a*. The lever 41 protrudes from the notch 40*d* formed on the outer circumferential surface 40*f* of the housing 40*a*. The lever 41 is rotatably attached to the housing 40*a* around the central axis O of the housing 40*a*. The lever 41 is rotatable around the central axis O along the notch 40*d* by approximately 90 degrees.

Figure 3:
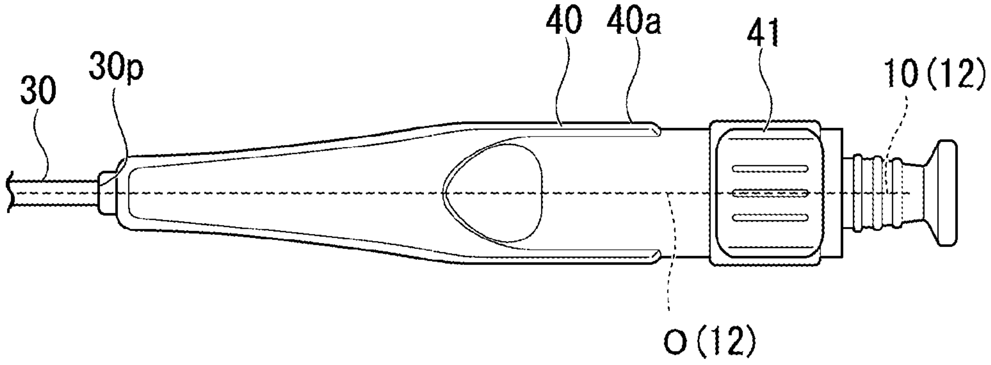
FIG. 3 is an enlarged view showing the operation portion of the stent delivery system in the state of releasing the guide catheter according to the embodiment of the present disclosure.
Figure 4:
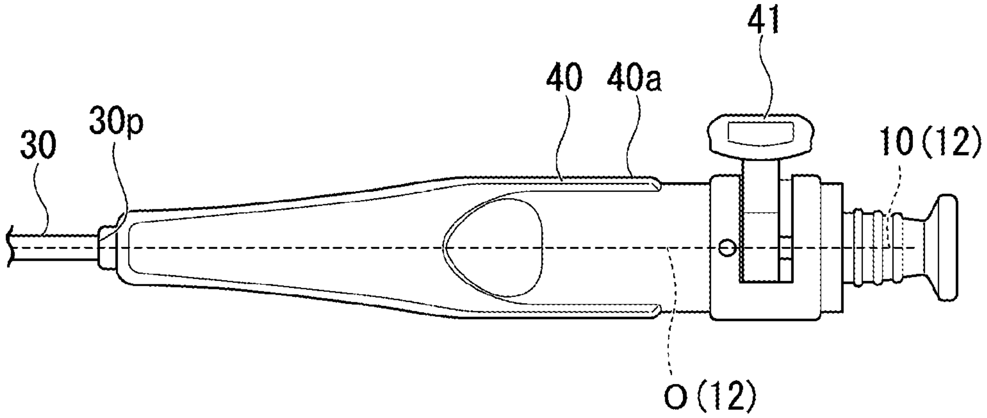
FIG. 4 an enlarged view showing the operation portion of the stent delivery system in a state of fixing the guide catheter according to the embodiment of the present disclosure.

FIG. 3 is a view showing a state in which the operation portion 40 has released the guide catheter 10 (released state). FIG. 3 shows the same state as that shown in FIG. 2. FIG. 4 is a view showing a state (fixed state) in which the operation portion 40 fixes the guide catheter 10. As shown in FIG. 3 and FIG. 4, the lever 41 rotates around the central axis O of the housing 40*a* to be able to switch between the released state and the fixed state of the guide catheter 10. In the released state, when the lever 41 rotates clockwise by approximately 90 degrees from the proximal-end side toward the distal-end side, the lever 41 enters the fixed state. In the fixed state, when the lever 41 rotates counterclockwise by approximately 90 degrees from the proximal-end side toward the distal-end side, the lever 41 enters the released state.

In the collet chuck 50, the collet portion 51 is fixed to the housing 40*a*, and the operation wire 12 is clamped by the collet portions 51 to be fixed to the housing 40*a*. The chuck nut 52 of the collet chuck 50 is operated by the lever 41. As shown in FIG. 2, the collet chuck 50 is arranged in the internal space 40*c* of the housing 40*a*. The collet chuck 50 is arranged on the distal-end side of the lever 41. The collet portion 51 of the collet chuck 50 and the chuck nut 52 are formed so as to be relatively advanceable and retractable. The collet portion 51 has a male screw portion (screw) 51*a* and a collet 51*b*.

The male screw portion 51*a* is formed in a substantially cylindrical shape. The male screw portion 51*a* is arranged such that the central axis CO overlaps with the central axis O of the housing 40*a*. The male screw portion 51*a* is fixed such that a relative position with respect to the housing 50*a* does not change. The male screw portion 51*a* has a hollow portion 51*c* and a male screw 51*d*. The hollow portion 51*c* is formed along the central axis CO. The male screw portion 51*a* is arranged such that the hollow portion 51*c* communicates with the distal-end side hollow portion 40*b* of the housing 40*a*. The operation wire 12 of the guide catheter 10 is inserted into the hollow portion 51*c*. The male screw 51*d* is formed on the outer circumferential surface of the male screw portion 51*a* along the central axis CO.

The collet 51*b* is formed in a protruding shape protruding from the end portion 51*e* on the proximal-end side of the male screw portion 51*a* toward the proximal-end side. In the present embodiment, four collets 51*b* are provided. The four collets 51*b* are arranged symmetrically with respect to the central axis CO along the outer circumference of the operation wire 12 of the guide catheter 10.

The collet 51*b* has an inner surface 51*f* and an outer surface 51*g*. The inner surface 51*f* faces the operation wire 12 of the guide catheter 10. The inner side surface 51*f* is along the central axis CO.

The outer surface 51*g* is formed on the opposite side to the inner surface 51*f* in the collet 51*b*. The outer side surface 51*g* has an outer circumferential tapered surface 51*h* and a chuck guide surface 51*i*. The outer circumferential tapered surface 51*h* is formed on the distal-end side, and is separated from the central axis CO as toward the proximal-end side. The chuck guide surface 51*i* is formed on the proximal-end side of the outer circumferential tapered surface 51*h*, and is inclined toward the central axis CO side as toward the proximal-end side.

The chuck nut 52 is formed in a substantially tubular shape. The chuck nut 52 is arranged such that the central axis NO overlaps with the central axis O of the housing 40*a*. The chuck nut 52 is rotatably supported around the central axis O. The operation wire 12 of the guide catheter 10 is inserted into the hollow portion of the chuck nut 52. The chuck nut 52 is formed integrally with the lever 41. The lever 41 protrudes from the proximal-end side of the outer circumferential surface of the chuck nut 52.

The chuck nut 52 has a female screw portion (screw) 52*a*, a tapered portion 52*b*, and a straight pipe portion 52*c*. The female screw portion 52*a* is formed on the distal-end side of the chuck nut 52. A female screw 52*e* is formed on the inner circumferential surface of the female screw portion 52*a*. The female screw 52*e* is screwed with the male screw 51*d* of the collet portion 51.

Figure 5:
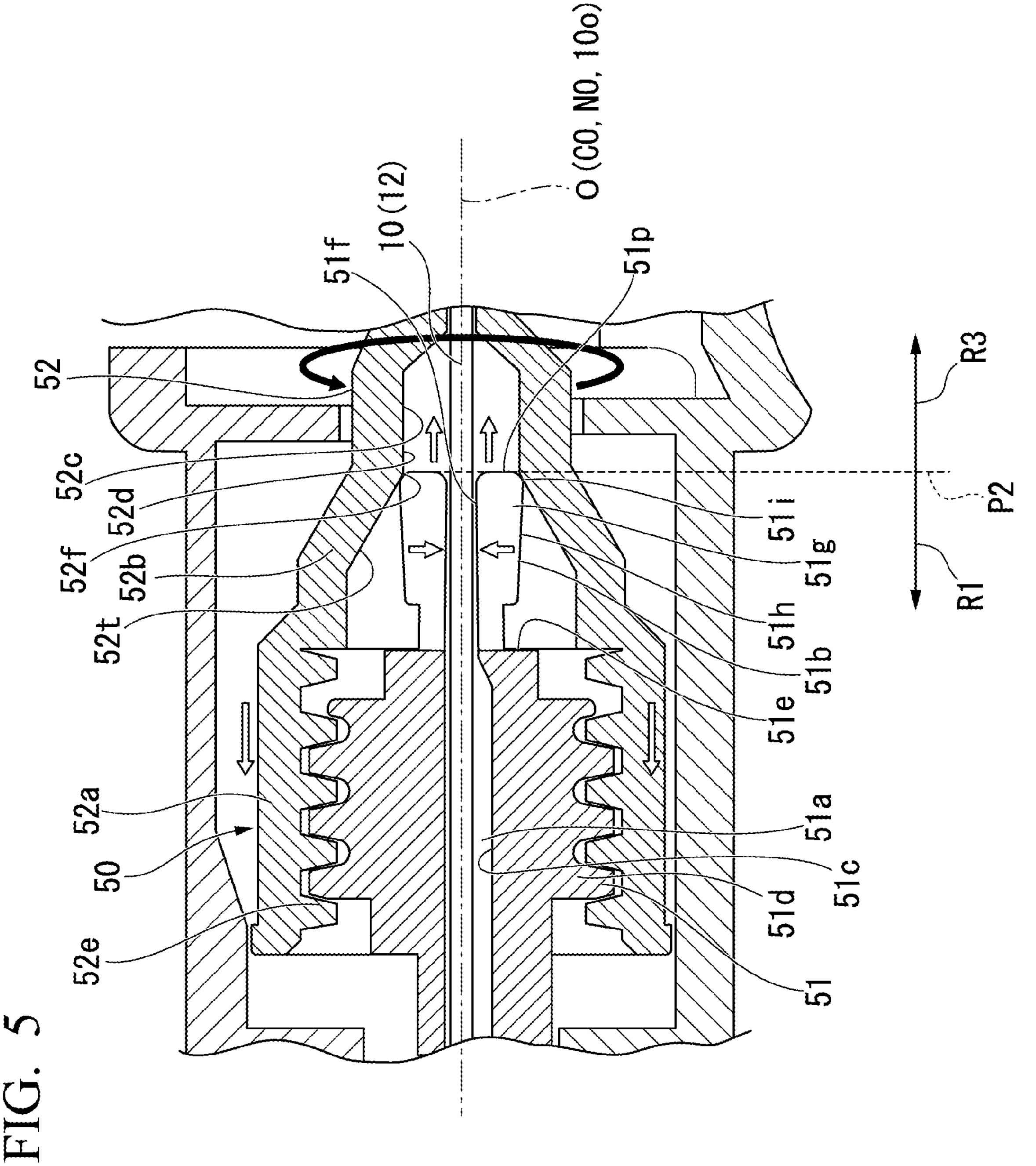
FIG. 5 is an enlarged cross-sectional view showing a collet chuck of the stent delivery system and a view of a first region according to the embodiment of the present disclosure.

The tapered portion 52*b* is formed on the proximal-end side of the female screw portion 52*a*. The tapered portion 52*b* has an inner circumferential tapered surface (inner circumferential surface) 52*t* on the inner circumferential surface on the proximal-end side. The diameter of the inner circumferential tapered surface 52*t* is reduced as toward the proximal-end side so as to be closer to the central axis NO side. As shown in FIG. 5, the inner circumferential tapered surface 52*t* is provided with a first region R1. The first region R1 is a region provided on the inner circumferential surface of the chuck nut 52, and the first region R1 is a region whose diameter is reduced as toward the proximal-end side so as to be closer to the central axis NO side.

As shown in FIG. 2, the straight pipe portion 52*c* is formed on the proximal-end side of the tapered portion 52*b*. The straight pipe portion 52*c* is formed in a cylindrical shape. The diameter of the straight pipe portion inner circumferential surface (inner circumferential surface) 52*d* of the straight pipe portion 52*c* is substantially constant. The straight pipe portion inner circumferential surface 52*d* is continuous with the inner circumferential tapered surface 52*t*.

Figure 6:
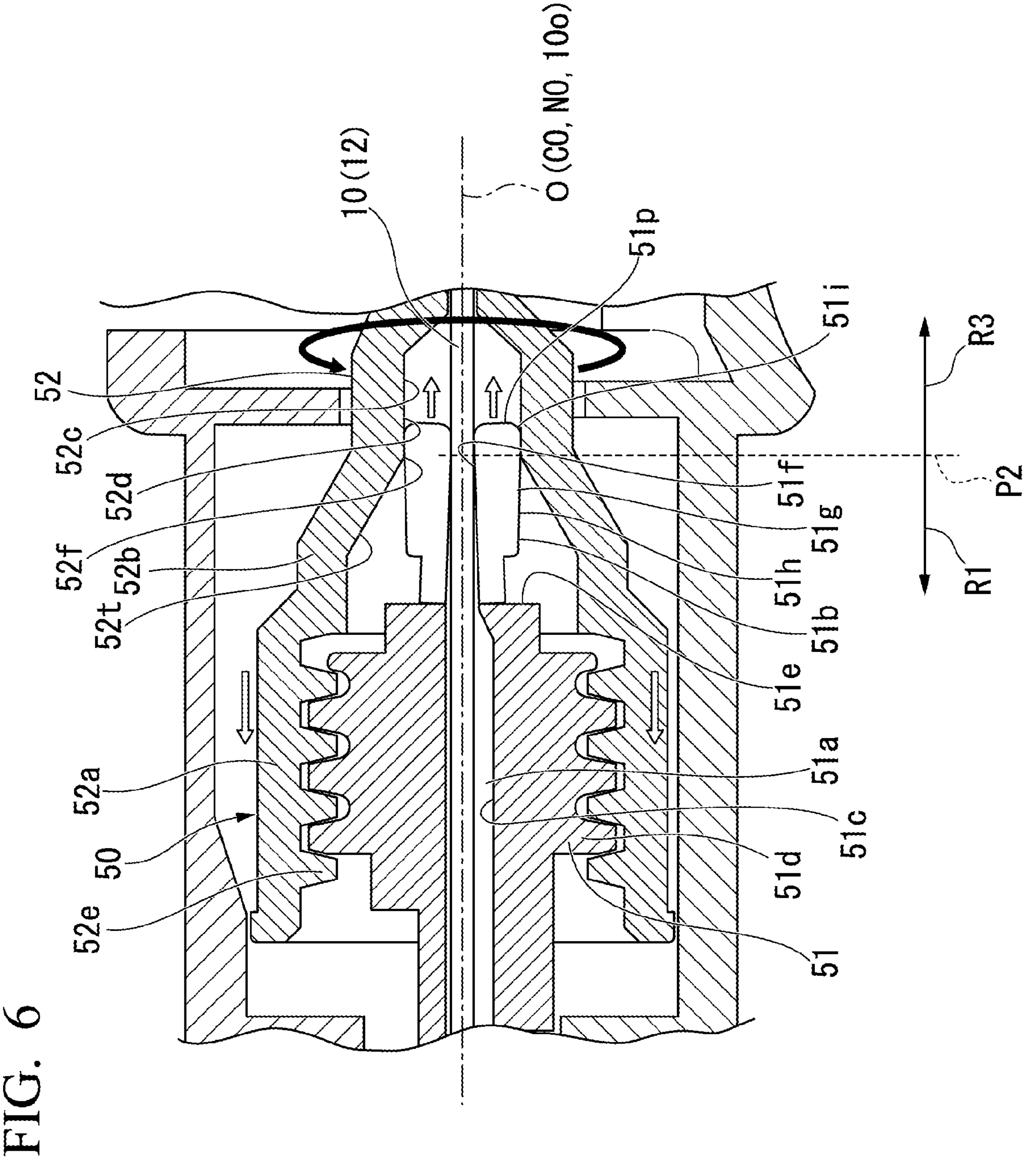
FIG. 6 is an enlarged cross-sectional view showing the collet chuck of the stent delivery system and a view of a second region according to the embodiment of the present disclosure.

As shown in FIG. 5 and FIG. 6, the straight pipe portion 52*c* is provided with a boundary position P2 and a second region R3. The boundary position P2 is a position provided on the inner circumferential surface of the chuck nut 52, and is a position of a boundary between the first region R1 and the second region R3. The boundary position P2 is provided at the end portion 52*f* on the distal-end side of the straight pipe portion inner circumferential surface 52*d* of the straight pipe portion 52*c*.

The second region R3 is a region provided on the inner circumferential surface of the chuck nut 52, and the second region R3 is a region in which the degree of diameter reduction as toward the proximal-end side so as to be closer to the central axis No side is gentler than that of the first region R1. According to the present embodiment, the diameter is not reduced in the second region R3. The second region R3 includes the boundary position P2. The second region R3 is provided on the inner circumferential surface 52*d* of the straight pipe portion 52*c*.

Next, the operations of adjusting the length L of the guide catheter 10 discharged from the distal end 30*t* of the pusher catheter 30 as shown in FIG. 1 will be described.

First, the user sets the length L to an appropriate length by pushing and pulling the operation wire 12 in the released state as shown in FIG. 2 and FIG. 3. In the released state, as shown in FIG. 2, the collet portion 51 and the chuck nut 52 are not in contact with each other (non-contact state).

The user rotates the lever 41 of the operation portion 40 around the central axis O of the housing 40*a* from the released state to the fixed state shown in FIG. 4. FIG. 5 is a view showing the collet chuck 50 when the lever 41 is rotated around the central axis O from the released state.

As shown in FIG. 5, when the lever 41 is rotated around the central axis O, the male screw 51*d* of the chuck nut 52 rotates with respect to the male screw 51*d* of the collet portion 51, and the chuck nut 52 approaches the collet portion 51.

When the chuck nut 52 approaches the collet portion 51, the collet 51*b* of the collet portion 51 and the inner circumferential surface of the chuck nut 52 come into contact with each other. First, the chuck guide surface 51*i* of the collet 51*b* and the inner circumferential tapered surface 52*t* of the chuck nut 52 come into contact with each other. The collet 51*b* comes into contact with the first region R1 of the chuck nut 52 (first contact state).

When the lever 41 is operated to approach the fixed state, the distal end 51*p* of the collet chuck 50 is bent toward the central axis O side of the housing 40*a* when the chuck nut 52 approaches the collet portion 51. When the chuck nut 52 approaches the collet portion 51 in the first contact state, the distal end 51*p* of the inner side surface 51*f* of the collet 51*b* is bent to approach the central axis O side of the housing 40*a*. When the chuck nut 52 approaches the collet portion 51 in the first contact state, the chuck guide surface 51*i* slides with respect to the inner circumferential tapered surface 52*t*, and the distal end 51*p* of the collet 51*b* is bent toward the central axis O side of the housing 40*a*.

When the chuck nut 52 is operated to approach the collet portion 51, the distal end 51*p* side of the inner side surface 51*f* of the collet 51*b* eventually comes into contact with the operation wire 12 of the guide catheter 10 and clamps the operation wire 12.

When the chuck nut 52 is operated to further approach the collet portion 51, the outer surface 51*g* of the collet 51*b* comes into contact with the end portion 52*f* on the distal-end side of the straight pipe portion inner circumferential surface 52*d* of the straight pipe portion 52*c* of the chuck nut 52. The collet 51*b* comes into contact with the boundary position P2 of the chuck nut 52.

When the collet 51*b* comes into contact with the boundary position P2, the collet 51*b* is tightened from the straight pipe portion inner circumferential surface 52*d* separated from the central axis 100 of the guide catheter 10 by a predetermined distance, and the distance between the distal end 51*p* of the inner surface 51*f* of the collet 51*b* and the central axis 100 becomes a predetermined distance. At the boundary position P2, the outer circumferential tapered surface 51*h* of the collet 51*b* is substantially parallel to the central axis O of the housing 40*a*. At the boundary position P2, the outer circumferential tapered surface 51*h* of the collet 51*b* is arranged on the central axis O side with respect to the straight pipe portion inner circumferential surface 52*d*. At the boundary position P2, the collet 51*b* clamps the operation wire 12 of the guide catheter 10 with a force of a predetermined magnitude.

When the chuck nut 52 is operated to further approach the collet portion 51, the collet 51*b* comes into contact with the second region R3 of the chuck nut 52 (second contact state).

In the stent delivery system 100 according to the present embodiment, the diameter of the straight pipe portion inner circumferential surface 52*d* is substantially constant, and the diameter is not reduced. Therefore, in the second contact state, when the chuck nut 52 approaches the collet portion 51, the distal end 51*p* of the inner surface 51*f* of the collet 51*b* is not bent toward the central axis 100 side of the guide catheter 10 and the distance therebetween is maintained.

FIG. 6 is a view showing the operations of the collet chuck 50 in the second region. As shown in FIG. 6, in the second region, the outer circumferential tapered surface 51*h* of the collet 51*b* is substantially parallel to the central axis O of the housing 40*a*. In the second region R3, the collet 51*b* clamps the operation wire 12 of the guide catheter 10 with a force of a predetermined magnitude.

In the second region R3, when the chuck nut 52 is operated to approach the collet portion 51, the lever 41 is eventually arranged at a position in the fixed state.

According to the stent delivery system 100 according to the present embodiment, the chuck nut 52 is provided with the first region R1 and the second region R3. Even if the chuck nut 52 is operated to approach the collet portion 51 in contact with the second region R3, the distal end 51*p* of the inner surface 51*f* of the collet 51*b* maintains the distance from the central axis 100 of the guide catheter 10 while clamping the operation wire 12. In the second region R3, the collet 51*b* clamps the operation wire 12 with a force of a predetermined magnitude. Therefore, the stent delivery system 100 can easily clamp the guide catheter 10 with the appropriate tightening force even if the relative positions of the collet 51*b* and the chuck nut 52 in the fixed state are displaced due to manufacturing variations or the like.

In the second region R3, the shape of the collet 51*b* is maintained such that the outer circumferential tapered surface 51*h* of the collet 51*b* is along the central axis O of the housing 40*a*. The shape of the collet 51*b* is maintained by the outer circumferential tapered surface 51*h* coming into contact with the straight pipe portion inner circumferential surface 52*d*. As a result, the distance between the inner surface 51*f* of the collet 51*b* and the central axis 100 of the guide catheter 10 is maintained at the predetermined distance. The distal end 51*p* of the inner surface 51*f* of the collet 51*b* clamps the operation wire 12 of the guide catheter 10 with the force of the predetermined magnitude. Therefore, the collet 51*b* clamps the guide catheter 10 with the appropriate tightening force in the second region R3 without forming a complicated shape.

The collet 51*b* has a chuck guide surface 51*i*. As a result, when the chuck nut 52 is operated to approach the collet portion 51 in the first region R1, the chuck guide surface 51*i* slides with respect to the inner circumferential tapered surface 52*t* of the chuck nut 52, and the distal end 51*p* of the collet 51*b* is easy to be bent toward the central axis O side of the housing 40*a*. Therefore, the collet chuck 50 can easily clamp the operation wire 12 of the guide catheter 10.

In the collet chuck 50, the collet 51*b* and the chuck nut 52 can relatively advance and retreat by forming the screw in the collet portion 51 and the chuck nut 52 for screwing them together. Therefore, when the collet 51*b* approaches the chuck nut 52 while being in contact with the chuck nut 52, it is easy for the user to make the collet 51*b* to approach thereto with a gentle force.

Since the collet portion 51 is fixed at an unchanged relative position with respect to the housing 40*a* extending from the pusher catheter 30, the collet portion 51 is fixed at an unchanged position with respect to the pusher catheter 30. Therefore, when the collet 51*b* clamps the operation wire 12 while the collet 51*b* and the chuck nut 52 are relatively close to each other in the second region R3, the collet 51*b* does not move the guide catheter 10 with respect to the pusher catheter 30.

The housing 40*a* has the lever 41. Therefore, it is easy for the user to relatively advance and retract the collet portion 51 and the chuck nut 52.

Although each embodiment of the present disclosure has been described in detail with reference to the figures, the specific configuration is not limited to this embodiment, and includes design changes in areas that do not deviate from the scope of the present invention. Further, the components shown in the above-described embodiment and the modification examples shown below can be appropriately combined and configured.

For example, the diameter of the inner circumferential surface of the straight pipe portion configuring the second region R3 does not have to be constant. The diameter of the inner circumferential surface of the straight pipe portion may be reduced more gently than the reduction of the diameter of the inner circumferential tapered surface 52*t* of the chuck nut forming the first region R1. If the degree of the reduction in the diameter of the inner circumferential surface of the straight pipe portion is gentler than the degree of the reduction in the diameter of the inner circumferential tapered surface 52*t*, in a case in which the chuck nut 52 approaches with respect to the collet portion 51, the amount of the distal end 51*p* of the inner side surface 51*f* being bent to approach the center axis 100 side is smaller in the second contact state than that in the first contact state. As a result, in a case in which the chuck nut 52 approaches the collet portion 51 in the second contact state, an increase in the force with which the collet 51*b* tightens the guide catheter 10 is suppressed. Therefore, even if the relative positions of the collet 51*b* and the chuck nut in the fixed state are displaced due to manufacturing variations or the like, the guide catheter 10 can be easily clamped with the appropriate tightening force.

Figure 7:
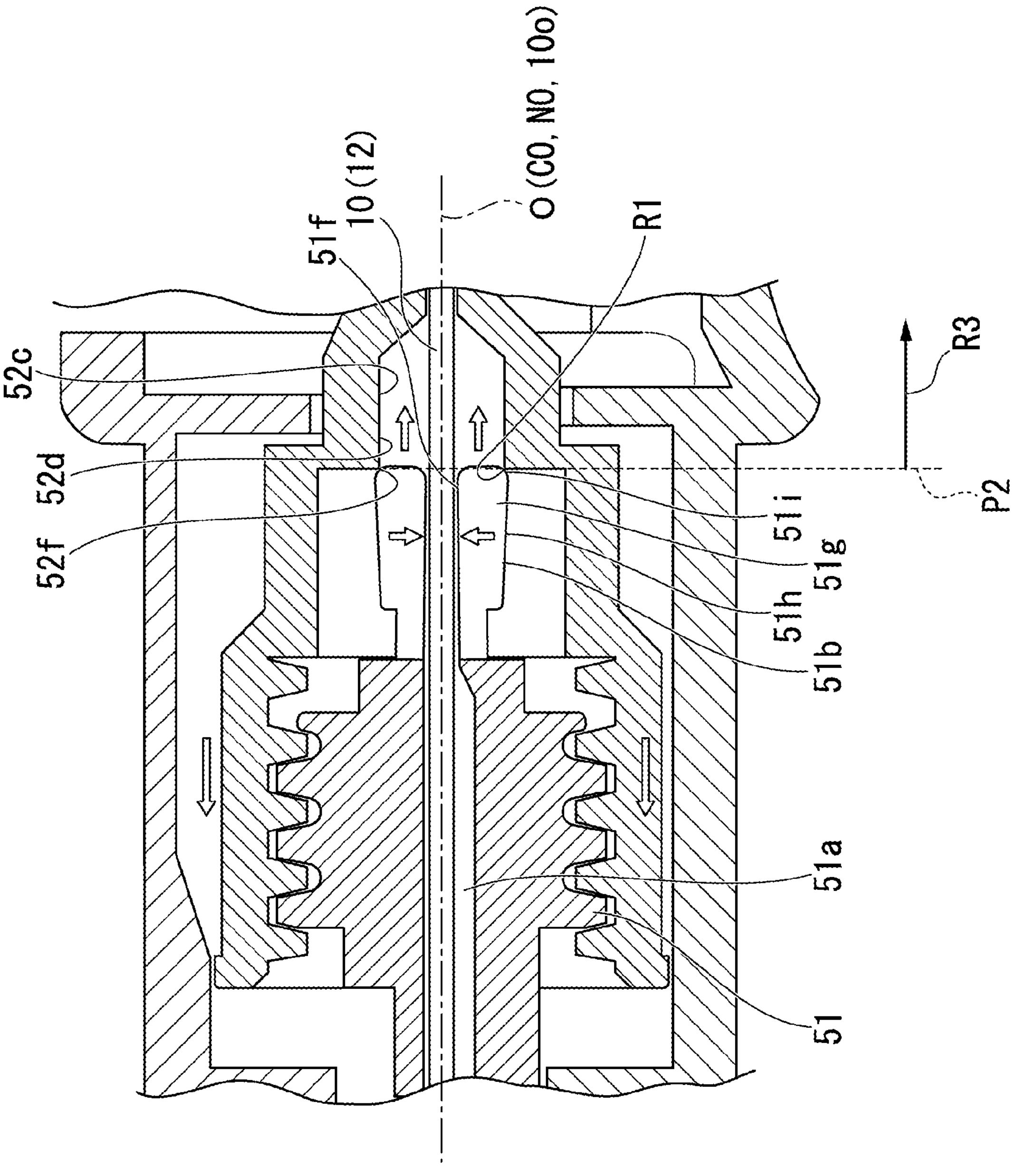
FIG. 7 is a cross-sectional view showing a modification example of the collet chuck according to the embodiment of the present disclosure.

As shown in FIG. 7, the collet chuck may not have the inner circumferential tapered surface 52*t*. The chuck guide surface 51*i* may be configured to abut on the corner of the end portion 52*f* of the straight pipe portion 52*c* without abutting on the inner circumferential tapered surface 52*t*. When the collet portion 51 and the chuck nut relatively approach each other in a state where the corner of the end portion 52*f* of the pipe portion 52*c* and the collet 51*b* are in contact with each other, the distal end 51*p* of the collet 51*b* may be bent to the central axis O side of the housing 40*a*. The definition of the first region R1 may be expanded to a region in which the distal end 51*p* is bent toward the central axis O when the approaching collet 51*b* is in contact therewith and the collet portion 51 and the chuck nut relatively approach each other.

Figure 8:
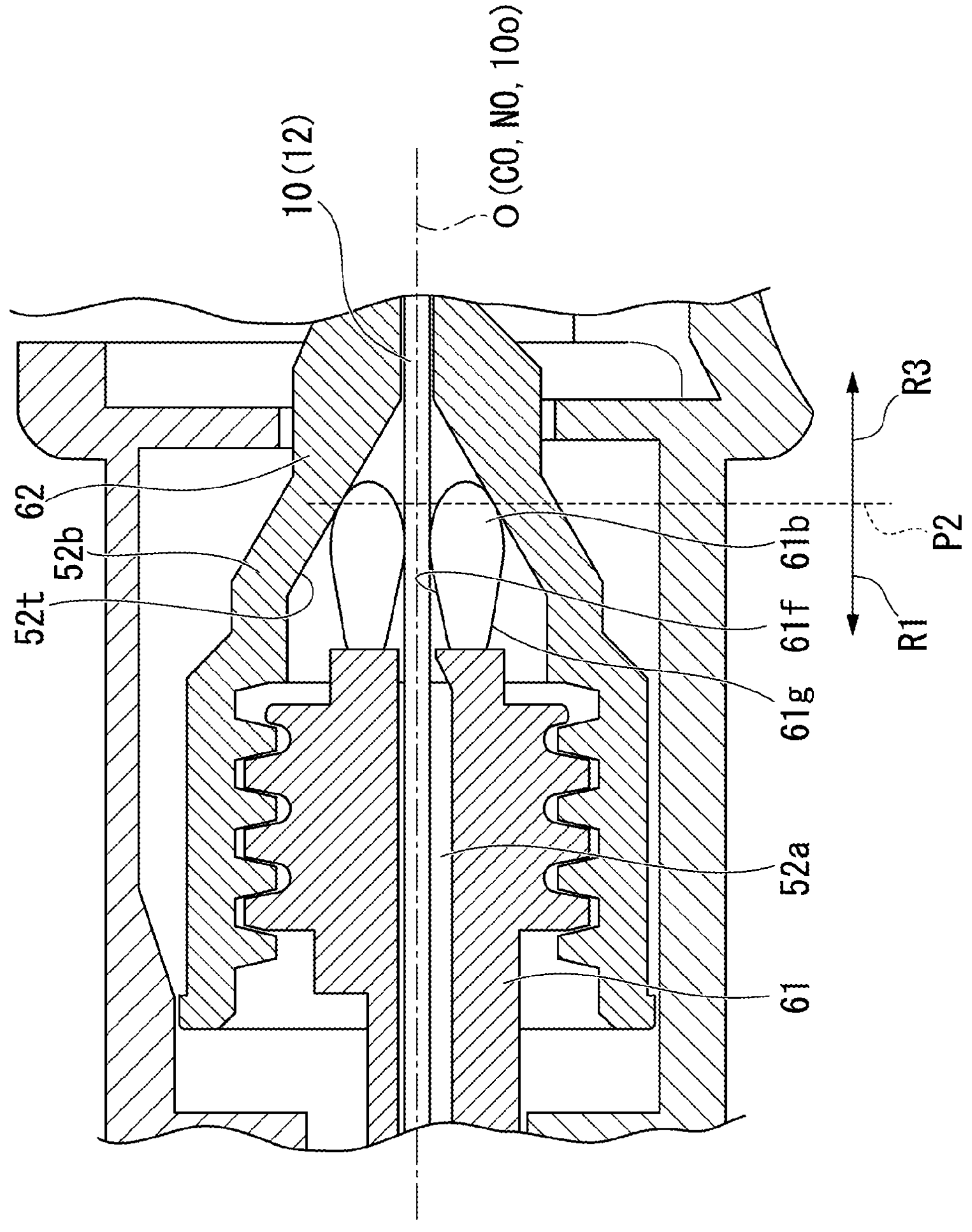
FIG. 8 is a cross-sectional view showing another modification example of the collet chuck according to the embodiment of the present disclosure.

As shown in FIG. 8, the collet chuck may not have the straight pipe portion 52*c*. An appropriate curvature may be formed on the inner surface 61*f* and the outer surface 61*g* of the collet portion 61, and the collet 61*b* may be operated to approach the chuck nut 62 while being in contact with the inner circumferential tapered surface 52*t* of the chuck nut 62. As a result, in a state in which the collet portion 51 and the chuck nut relatively approach each other in a state where the collet 51*b* and the chuck nut 62 are in contact with each other on the proximal-end side of the first region R1, the bending amount of the distal end 51*p* toward the central axis O side may be smaller than that in the first region R1. As a result, the collet chuck may clamp the guide catheter 10 with the appropriate tightening force. The definition of the second region R3 may be expanded to a region in which the bending amount of the distal end 51*p* is smaller than that in the first region R1 when the collet 51*b* is in contact therewith and the collet portion 51 and the chuck nut relatively approach each other.

The number of collets is not limited to four. The collet may be one, and there may be two or more collets.

The lever may be configured to enter the released state when the lever is rotated counterclockwise from the proximal-end side to the distal-end side, and to enter the fixed state when the lever is rotated clockwise. The lever may not have the rotatable range of 90 degrees.

The guide catheter may not have the operation wire 12. In that case, only the catheter lumen configures the guide catheter, and the operation portion 40 clamps the catheter lumen. A guide wire port is formed on the outer circumferential surface of the guide catheter, and the guide wire G is discharged from the guide wire port.

Although embodiments and modification examples of the present disclosure have been described above in detail with reference to the drawings, the specific configuration is not limited to the embodiment, and also includes various modifications. The present disclosure is not limited to the aforementioned embodiments and modification examples, but is only limited by the appended claims.

What is claimed is:

1. A stent delivery system, comprising:

a stent;

a pusher catheter disposed at a proximal-end side of the stent;

a guide catheter insertable into the stent and the pusher catheter; and a collet chuck disposed at the proximal-end side of the pusher catheter, wherein the collet chuck comprises:

a collet disposed along an outer circumference of the guide catheter; and a chuck nut provided to be relatively advanceable and retractable with respect to the collet and into which the guide catheter is insertable, wherein an inner circumferential surface of the chuck nut has a first region and an adjacent second region, wherein the first region is tapered, wherein the second region is non-tapered, wherein the first region and the second region are physically connected and configured to make direct contact with an outer circumferential surface of the collet, and wherein the first region and the second region are continuous with each other such that the first region and the second region are fixed relative to each other.

2. The stent delivery system according to claim 1, wherein a diameter of the first region is reduced toward the proximal-end side, and wherein a degree of diameter reduction toward the proximal-end side in the second region is lower than a degree of diameter reduction toward the proximal-end side in the first region.

3. The stent delivery system according to claim 2, wherein when the collet is not in contact with the chuck nut, an inner surface facing the guide catheter is along a center axis of the collet chuck, and an outer surface on an opposite side of the inner surface includes an outer circumferential tapered surface separating from the center axis of the collet chuck as being closer to the chuck nut.

4. The stent delivery system according to claim 3, wherein the chuck nut is formed in a substantially tubular shape.

5. The stent delivery system according to claim 3, wherein the inner circumferential surface includes:

an inner circumferential tapered surface having the first region; and a straight pipe portion inner circumferential surface being continuous to the inner circumferential tapered surface and having the second region, the straight pipe portion inner circumferential surface being formed on an inner side of a cylindrical straight pipe portion which is formed at the proximal-end side.

6. The stent delivery system of claim 5, wherein the collet chuck is configured such that as the collet and the chuck nut approach each other, the outer surface of the collet and the first region of the inner circumferential tapered surface of the chuck nut come into contact with each other, and the outer circumferential tapered surface of the collet and the second region of the straight pipe portion inner circumferential surface of the chuck nut come into contact with each other.

7. The stent delivery system according to claim 3, wherein the outer surface includes a chuck guide surface formed at the chuck nut side to be continuous to the outer circumferential tapered surface and being inclined toward the center axis side of the collet chuck as being closer to the chuck nut, and wherein the chuck guide surface of the collet and the first region of the inner circumferential tapered surface of the chuck nut are in contact with each other.

8. The stent delivery system according to claim 1, wherein in the collet chuck, one or more screws are formed in the collet and the chuck nut, and wherein the collet and the chuck nut relatively rotate with each other such that the collet and the chuck nut relatively advance and retract with each other.

9. The stent delivery system according to claim 1, wherein the collet is arranged such that a relative position with respect to the pusher catheter is unchanged.

10. The stent delivery system according to claim 1, wherein the chuck nut includes a lever protruding from an outer circumferential surface.

11. The stent delivery system according to claim 10, further comprising:

a housing to which the collet is fixed, wherein the guide catheter is switched between a fixed state and a released state by rotating the lever with respect to the housing at approximately 90 degrees.

12. The stent delivery system according to claim 1, wherein in the chuck nut, the second region of the inner circumferential surface is parallel to a center axis of the guide catheter.

13. The stent delivery system according to claim 1, wherein the guide catheter is insertable into a channel of an endoscope, and a guide wire is insertable into the guide catheter.

14. The stent delivery system according to claim 13, wherein the guide catheter comprises:

a catheter lumen disposed in the stent; and an operation wire connected to the catheter lumen, wherein the collet chuck is configured to clamp the operation wire.

15. The stent delivery system according to claim 1, wherein the outer circumferential surface of the collet is inclined toward a center axis of the guide catheter when moving distally from a proximal end side to a distal end side of the outer circumferential surface of the collet when the collet is in contact with the first region, and the outer circumferential surface of the collet is parallel to the center axis when the collet is in contact with the second region.

16. The stent delivery system according to claim 1, wherein a diameter of the first region is reduced toward the proximal-end side, wherein an outer diameter of the collet is increased toward the proximal-end side when moving distally from a proximal end side to a distal end side of the outer circumferential surface of the collet when the collet is in contact with the first region, and the outer circumferential surface of the collet is parallel to a center axis of the guide catheter when the collet is in contact with the second region.

* * * * *